United States Patent [19]

Kramer et al.

[11] Patent Number: 4,939,146

[45] Date of Patent: Jul. 3, 1990

[54] METHOD FOR ALLEVIATING ISCHEMIC-REPERFUSION INJURY

[76] Inventors: Richard S. Kramer, 24F - 1315 Morreene Rd., Durham, N.C. 27705; Robert D. Pearlstein, 2901 Arnold Rd., Durham, N.C. 27707

[21] Appl. No.: 53,468

[22] Filed: May 26, 1987

Related U.S. Application Data

[63] Continuation-in-part of Ser. No. 8,378, Jan. 29, 1987, abandoned.

[51] Int. Cl.$^5$ ............................................ A61K 31/048
[52] U.S. Cl. ...................................... 514/724; 514/730; 514/738
[58] Field of Search ........................ 514/724, 730, 738

[56] References Cited

U.S. PATENT DOCUMENTS

| | | |
|---|---|---|
| 3,749,783 | 7/1973 | Berger et al. |
| 3,788,468 | 1/1974 | Gainer |
| 3,853,993 | 12/1974 | Gainer |
| 3,953,595 | 4/1976 | Holland |
| 3,975,519 | 8/1976 | Gainer |

FOREIGN PATENT DOCUMENTS 8600812  2/1986  World Int. Prop. O.

OTHER PUBLICATIONS

Lucchesi et al., "Leukocytes and Ischemia-induced Myocardial Injury", Ann. Rev. Pharmacol. Toxicol. 26:201–224, 1986.
Hofmann et al., "The influence of reperfusion on infarct size after experimental coronary artery occlusion", Basic Res. Cardiol, 75:572–582, 1980.
Arfors et al., PCT Application No. WO 86/00812 dated Feb. 13, 1986.
J. C. Livesey et al., Radiation–Protective Drugs and Their Reaction Mechanisms, Noyes Publications, Park Ridge, N.J., 1985, pp. 62–64.
W. A. Cramp, Radiation Protection of Shigella Flexneri Y6R by Ethanol, B-mercaptoethanol and Several Polyhydric Alcohols, Int. J. Radiat. Biol. 15:227–232, 1969.
T. Sanner and A. Pihl, Significance and Mechanism of the Indirect Effect in Bacterial Cells, The Relative Protective Effect of Added Compounds in Escherichia coli B, Irradiated in Liquid and in Frozen Suspensions, Radiation Research 37:216–227, 1969.
S. R. Jolly et al., "Canine Myocardial Reperfusion Injury Its Reduction by the Combined Administration of Superoxide Dismutase and Catalase", Circulation Research, vol. 54, No. 3, Mar. 1984, pp. 227–285.
"Drugs May Help Revive Brain Dead", Asscociated Press, The Cincinnati Post, Thursday, Oct. 2, 1986.
R. Del Maestro, "Systemic Consequences of $O_2$ Production", Section 49 of Methods in Enzymology, vol. 105, (1984), Academic Press.
"Oxidation of OH Scavengers and Alcohols", Section 68 of Methods in Enzymology, vol. 105, pp. 517–518, (1984) Academic Press.
Bo K. Siesjo, "Review Cell Damage in the Brain: A speculative Synthesis", Journal of Cerebral Blood Flow and Metabolism, 1:155–185, 1981 Raven Press, New York.
P. O. Seglen, "Preparation of Rat Liver Cells III, Enzymatic Requirements for Tissue Dispersion", Experimental Cell Research 82 (1973) pp. 391–398.
Chien et al., "Microsomal Membrane Dysfunction in Ischemic Rat Liver Cells", Abstract of Biochemistry and Biophysics 180, 191–198 (1977).
Marubayashi et al., "Role of Free Radicals in Ischemic Rat Liver Cell Injury: Prevent Damage by alpha-tocopherol Administration", Surgery vol. 90, No. 2, Feb. 1986, pp. 184–191.
Lyon et al., "Relationship Between Alcohol Intoxification and the Ordering of Brain Membranes by A Series of Short-Chain Alcohols", Journal of Pharmocology and Experimental Therapeutics, vol. 218, No. 3, 1981, pp. 669–675.
Dorfman et al., "Reactivity of the Hydroxyl Radical in Aqueous Solutions", U.S. Dept. of Commerce, National Bureau of Standards, (1973).
Ambrosio et al., "Reduction in Experimental Infarct Size by Recombinant Human Superoxide Dismutose:Insights into the Pathophysiology of Reperfusion Injury", Circulation 74, No. 6, 1424–1433, 1986.
Sakurai et al., Chem Abst. 106(13):95942c (1987).
Arfors et al., Chem. Abst. 104(26):230491f (1986).
Bernauer, Walter, Chem. Abst. 105(15):12959g (1986).
Raleigh et al., Chem. Abst. 99(23):190652d (1983).
Cohen et al., Chem. Abst. 86(1):656u (1977).

Primary Examiner—Douglas W. Robinson
Assistant Examiner—Zohreh A. Fay
Attorney, Agent, or Firm—Finnegan, Henderson, Farabow, Garrett & Dunner

[57] ABSTRACT

A method for alleviating ischemic-reperfusion injury in a mammal which has suffered from a disease condition resulting from a deprivation of oxygen comprising the step of administering to the mammal alone, or in combination, an effective amount of an aliphatic alcohol having from 2 to 6 carbon atoms, a phenylalcohol having from 7 to 12 carbon atoms wherein the alcohol portion of the phenylalcohol has 1 or 2 carbon atoms, sorbitol and/or a polyol phosphate having from 3 to 9 carbon atoms or a salt thereof prior to or during the restoration of oxygen to alleviate ischemic-reperfusion injury.

6 Claims, No Drawings

METHOD FOR ALLEVIATING ISCHEMIC-REPERFUSION INJURY

This application is a continuation-in-part of Application Ser. No. 008,378, filed Jan. 29, 1987 now abandoned.

BACKGROUND OF THE INVENTION

The present invention relates to a method for alleviating ischemic-reperfusion injury in a mammal which has suffered from a disease condition resulting from a deprivation of oxygen.

It is well-known that cell damage occurs in mammals which have been deprived of oxygen. Brain cell damage following a stroke or cardiac arrest is but one example of such cell damage.

In recent years, it has been determined that such cell damage most likely occurs during the recirculation period, that is, when blood is recirculated to a cell previously deprived of oxygen. See, for example, B. K. Siesjo, "Review-Cell Damage in the Brain: A Speculative Synthesis," Journal of Cerebral Blood Flow and Metabolism, 1:155-185; 1981 Raven Press, New York.

The term "ischemic-reperfusion injury" refers to such damage, that is, damage which occurs during the recirculation period following oxygen deprivation. A treatment for alleviating such ischemic-reperfusion injury is highly desirable and much sought after.

SUMMARY OF THE INVENTION

It is, therefore, a main object of the present invention to provide a method for alleviating ischemic-reperfusion injury in a mammal which has suffered from a disease condition resulting from a deprivation of oxygen.

It is a more specific object of the present invention to provide a method for alleviating ischemic-reperfusion injury in a mammal which has suffered from hypoxia or ischemia such as that which occurs in cardiac arrest, pulmonary embolus, renal artery occlusion, coronary occlusion or occlusive stroke.

It is a further object of the present invention to provide a method for alleviating ischemic-reperfusion injury in a mammal which has suffered from anoxia such as occurs as a result of suffocation or profound anemia.

Additional objects and advantages of the invention will be set forth in part in the description which follows, and in part will be apparent from the description, or may be learned by practice of the invention. The objects and advantages of the invention may be realized and obtained by means of instrumentalities and combinations particularly pointed out in the appended claims.

To achieve the objects and in accordance with the purpose of the invention, as embodied and broadly described herein, the invention comprises a method for alleviating ischemic-reperfusion injury in a mammal which has suffered from a disease condition resulting from a deprivation of oxygen comprising the step of administering to the mammal an effective amount of a primary aliphatic alcohol having from 2 to 6 carbon atoms prior to or during the restoration of oxygen to alleviate ischemic-reperfusion injury.

To further achieve the objects and in accordance with the purpose of the invention, as embodied and broadly described herein, the invention further comprises a method for alleviating ischemic-reperfusion injury in a mammal which has suffered from a disease condition resulting from a deprivation of oxygen comprising the step of administering to the mammal an effective amount of a phenylalcohol having from 7 to 12 carbon atoms, wherein said alcohol portion of said phenylalcohol has 1 or 2 carbon atoms, prior to or during the restoration of oxygen to alleviate ischemic-reperfusion injury.

To further achieve the objects and in accordance with the purpose of the invention, as embodied and broadly described herein, the invention further comprises a method for alleviating ischemic-reperfusion injury in a mammal which has suffered from a disease condition resulting from a deprivation of oxygen comprising the step of administering to said mammal an effective amount of sorbitol prior to or during the restoration of oxygen to alleviate ischemic-reperfusion injury.

To further achieve the objects and in accordance with the purpose of the invention, as embodied and broadly described herein, the invention further comprises a method for alleviating ischemic-reperfusion injury in a mammal which has suffered from a disease condition resulting from a deprivation of oxygen comprising the step of administering to said mammal an effective amount of a polyol phosphate having from 3 to 9 carbon atoms or a salt thereof prior to or during the restoration of oxygen to alleviate ischemic-reperfusion injury.

The foregoing and other objects, features, and advantages of the present invention will be made more apparent from the following description of the preferred embodiment.

DESCRIPTION OF THE PREFERRED EMBODIMENTS

Reference will now be made in detail to present preferred embodiments of the invention.

A method for alleviating ischemic-reperfusion injury in a mammal which has suffered from a disease condition resulting from deprivation of oxygen in accordance with the present invention comprises the step of administering to said mammal an effective amount of a therapeutic agent of the present invention prior to or during the restoration of oxygen to alleviate ischemic-reperfusion injury.

As embodied herein, the term "ischemic-reperfusion injury" refers to damage to an oxygen-deprived cell which occurs during the recirculation period when the cell is resupplied with oxygen. Further, the expression "alleviating" ischemic-reperfusion injury means the reduction and/or elimination of such injury.

By disease conditions resulting from a deprivation of oxygen, it is meant conditions such as hypoxia or ischemia (i.e., the partial or total loss of blood supply to the body as a whole, an organ within the body or a region within an organ, such as occurs in cardiac arrest, pulmonary embolus, renal artery occlusion, coronary occlusion or occlusive stroke). The term disease conditions resulting from a deprivation of oxygen is also meant to include conditions such as anoxia (i.e., inadequate provision of oxygen despite continued circulation which occurs in suffocation or profound anemia).

In accordance with a first embodiment of the present invention, the therapeutic agent for alleviating ischemic-reperfusion injury is a primary aliphatic alcohol having from 2 to 6 carbon atoms. Preferably, the aliphatic alcohol is a primary aliphatic alcohol selected from the group of ethanol, n-propanol, n-butanol, and n-pentanol. As will be illustrated in the examples which follow, these primary aliphatic alcohols are unexpectedly superior in alleviating ischemic-reperfusion injury to closely related analogues and homologues. Of these primary aliphatic alcohols, the preferred therapeutic agent for alleviating ischemic-reperfusion injury is ethanol.

In accordance with a second embodiment of the present invention, the therapeutic agent for alleviating ischemic-reperfusion injury is a phenylalcohol having from 7 to 12 carbon atoms wherein the alcohol portion of the phenylalcohol has 1 or 2 carbon atoms. As embodied herein, a preferred phenylalcohol therapeutic agent for alleviating ischemic-reperfusion injury in accordance with the present invention is 2-phenylethanol. It is contemplated that various derivatives of 2-phenylethanol will also have activity in alleviating ischemic-reperfusion injury. For example, substitution of various groups on the phenyl ring could favorably influence the phenylalcohol's affinity for the binding site and/or possibly reduce any inherent toxicity of the phenylalcohol. A representative but not exhaustive list of possible substituents on the phenyl ring of the phenylalcohol include methyl, ethyl, methoxy, ethoxy, nitro, hydroxy, or thiol groups, or combinations thereof on any of the five available carbon atoms of the phenyl ring. In accordance with this second embodiment of the present invention, however, it is critical that the alcohol portion of the phenylalcohol have only 1 or 2 carbon atoms. As illustrated in the examples which follow, phenylpropanol and phenylbutanol (i.e., phenylalcohols having alcohol portions of 3 and 4 carbon atoms respectively) are not active in alleviating ischemic-reperfusion injury.

In accordance with a third embodiment of the present invention, the therapeutic agent for alleviating ischemic-reperfusion injury is sorbitol.

In accordance with a fourth embodiment of the present invention, the therapeutic agent for alleviating ischemic-reperfusion injury is a polyol phosphate having from 3 to 9 carbon atoms or a salt thereof. As embodied herein, the term polyol phosphate refers to an organic phosphate compound having three or more hydroxyl groups as well as derivatives thereof including, but not limited to, derivatives wherein one or more of the hydroxyl groups have been substituted for by esterification, nitration or amination. Preferred polyol phosphate therapeutic agents for alleviating ischemic-reperfusion injury in accordance with the present invention are sorbitol-6-phosphate and mannitol-1-phosphate. Preferably, the polyol phosphate therapeutic agents of the present invention are administered as salts in aqueous solution.

For purposes of the present invention, the above-described therapeutic agents for alleviating ischemic-reperfusion injury are administered prior to or during the restoration of oxygen. Preferably, the therapeutic agents will be administered, either alone or in combination, as intravenous infusions administered acutely after the hypoxic, ischemic, or anoxic condition occurs. For example, the therapeutic agent of the present invention can be administered by intravenous infusion immediately after a cerebral infarction, a myocardial infarction, asphyxia, or a cardiopulmonary arrest. Alternatively, if the condition of the patient permits, the therapeutic agents of the present invention could be administered orally, for example, down a gastric tube. Another method of administration which could sometimes be used is arterial perfusion with a catheter. This latter method of administration is advantageous since it allows for a higher concentration of the therapeutic agent to reach the target organ and a lower concentration to be delivered to the body as a whole.

The therapeutic agents of the present invention could also be used prophylatically in surgical settings where circulation to an organ or organ system is deliberately and/or transiently interrupted, for example, carotid endarterctomy, coronary artery bypass, grafting, organ transplanting, etc.

The concentration of therapeutic agent which should be administered will of course vary depending upon the particular therapeutic agent employed and the method of administration. With ethanol, for example, if the ethanol is being administered by intravenous infusion, preferably a concentration of 5-15% ethanol is used. Too low a concentration (i.e., less than 5% ethanol) is undesirable because it requires the introduction of too much water into the patient. On the other hand, too high a concentration (i.e., above 15% ethanol) is also undesirable because it can cause sclerosis of the vein. However, if the ethanol is administered orally, for example, down a gastric tube, then a much higher concentration of ethanol (up to 40%) could be tolerated by a patient. The ethanol can be diluted with standard diluents known in the art such as physiologic saline or 5% dextrose in water.

In administering the therapeutic agents of the present invention, preferably a large volume loading dose is used at the start of the treatment. Then the treatment is continued with a maintenance dose. Further administration can then be determined by monitoring at intervals the levels of the therapeutic agent in the blood.

The amount of therapeutic agent which should be administered and the duration of administration will also vary depending upon the concentration of the particular therapeutic agent employed and the method of application. In accordance with a preferred embodiment of the present invention, wherein a 10% ethanol solution is administered by intravenous infusion, a large volume loading dosage of from 5 to 10 ml/kg of body weight is first administered over a period of 30 minutes. Thereafter a maintenance dose of 3 to 5 ml/kg of body weight per hour is administered for 4–6 hours. Further administration of ethanol is then determined by monitoring the blood ethanol level in order to maintain a blood ethanol level of between 150 and 400 mg. per 100 ml. of blood.

The suitability of the therapeutic agents of the present invention for alleviating ischemic-reperfusion injury in a mammal which has suffered from a disease condition resulting from a deprivation of oxygen can be predicted from the following examples which utilize a scientifically accepted in vitro model of ischemic-reperfusion injury. This in vitro model of ischemic-reperfusion injury is described in Example 1.

EXAMPLE 1

Rat hepatic cells are isolated by the method described in P. O. Seglen, "Preparation of Rat Liver Cells," Experimental Cell Research 82 (1973) 391–398. The rat hepatic cells were then suspended in a modified Krebs-Henseleit (K-H) medium containing NaCl 144 mM, KCl 5 mM, NaHCO$_3$ 5 mM, MgSO$_4$ 1.3 mM, NaH$_2$PO$_4$ 1.0 mM, CaCl$_2$ 1.3 mM, supplemented with glucose 20 mM, pyruvate 5 mM, 1% bovine serum albumin, and N-2-hydroxyethylpiperazine-N'-2-ethane- sulfonic acid (HEPES), at a pH of 7.4, and at a concentration of 20 mg hepatocyte protein/ml medium. Cell suspensions were preincubated for 1 hour at 23° C., with gentle agitation, in plastic centrifuge tubes.

Anaerobiosis was instituted by flushing the gas phase with argon and then permitting the cells to consume the residual oxygen in the medium. Anaerobiosis was attained within 3 minutes as determined polargraphically. The anaerobic suspensions were maintained in a 37° C. water bath without agitation. After two hours, a post-anaerobic viability measurement was taken. Approximately 75% of the hepatocytes were viable after two hours of anaerobic incubation, using two critiera, retention of cytosolic lactate dehydrogenase and exclusion of trypan blue.

The hepatocytes were then gently resuspended and a 1 ml aquilot of the stock suspension was added to 9 ml of aerated medium in which various therapeutic agents of the present invention had been previously solubilized. Untreated control hepatocytes were also maintained. Suspensions were maintained for an additional four hours at 37° C. with gentle agitation, sufficient to maintain medium [$O_2$] in excess of 100 uM.

During the first 2-3 hours of aerobic incubation, the cell viability measurements were taken every 30 minutes using the same two criteria. The ultimate extent of cell loss four hours after resuspension in the oxygenated medium was also measured using the same two criteria. The data for the control where no therapeutic agent of the present invention was used (see untreated sample of Example 2) is consistent with values previously reported for in vivo rat liver reperfused after a comparable interval of complete ischemia. See K. R. Chin et al., "Microsomal Membrane Dysfunction in Ischemic Rat Liver Cells," Abstracts of Biochemistry and Biophysics 180, 191-198 (1977).

EXAMPLE 2

Using the procedure set forth in Example 1, the survival of untreated hepatocytes was compared with the survival of hepatocytes treated with various agents. Measurements from 1 to 39 observations were recorded. The mean surviving fraction of hepatocytes were as follows:

| TREATMENT | CONCEN-TRATION | NO. OF RECORDED MEASURE-MENTS | MEAN SURVIVING FRACTION |
| --- | --- | --- | --- |
| untreated | — | 39 | 30.63 ± 6.72% |
| ethanol | 20 mM | 39 | 64.83 ± 11.25% |
| methanol | 20 mM | 4 | 43.85 ± 10.22% |
| n-propanol | 20 mM | 4 | 69.40 ± 11.51% |
| n-butanol | 20 mM | 6 | 74.50 ± 10.55% |
| n-butanol | 100 mM | 1 | 31.50% |
| n-pentanol | 5 mM | 5 | 71.94 ± 9.57% |
| n-pentanol | 20 mM | 4 | 52.95 ± 13.22% |
| n-hexanol | 5 mM | 5 | 51.48 ± 19.05% |
| n-hexanol | 20 mM | 3 | 12.20 ± 11.96% |
| n-octanol | 5 mM | 1 | 0.00% |

The above data illustrates that between 5 and 20 mM concentrations of primary aliphatic alcohols having 2 to 6 carbon atoms were useful in alleviating ischemic-reperfusion injury in rat hepatic cells. These therapeutic agents were superior to their 8 carbon atom homolog (n-octanol). Indeed, the 8 carbon atom primary aliphatic alcohol apparently contributed to cell death. This is probably due to a secondary response of the more lipophilic alcohol vis a vis a tendency to disorder membrane structure. See E. C. Lyon et al., "Relationship between Alcohol Intoxication and the Disordering of Brain Membranes by a Series of Short-Chain Alcohols," J. Pharmacology & Experimental Therapeutics, Vol. 218, No.3, pp. 669-675 (1981). Methanol also showed some improvement over the untreated control. However, the known toxicity of methanol would preclude its use in alleviating ischemic-reperfusion injury.

EXAMPLE 3

Using the procedure set forth in Example 1, the survival of untreated hepatocytes was compared with the survival of hepatocytes treated with various concentrations of ethanol. Measurements from one (1) observation were recorded. The mean surviving fraction of hepatocytes were as follows:

| TREATMENT | CONCEN-TRATION | NO. OF RECORDED MEASURE-MENTS | MEAN SURVIVING FRACTION |
| --- | --- | --- | --- |
| untreated | — | 1 | 26.9% |
| ethanol | 20 mM | 1 | 54.0% |
| ethanol | 100 mM | 1 | 51.2% |
| ethanol | 250 mM | 1 | 45.8% |
| ethanol | 500 mM | 1 | 40.50% |
| ethanol | 750 mM | 1 | 29.5% |
| ethanol | 1000 mM | 1 | 0.0% |

The above data illustrates the effectiveness of ethanol, a preferred therapeutic agent of the present invention, in alleviating ischemic-reperfusion injury at a variety of concentrations. The most effective concentration tested was 20 mM. Higher concentrations were less effective and in the case of the highest concentration (1000 mM), the ethanol apparently contributed to cell death.

EXAMPLE 4

Using the procedure set forth in Example 1, the survival of untreated hepatocytes was compared with the survival of hepatocytes treated with various agents. Measurements from one (1) observation were recorded. The mean surviving fraction of hepatocytes were as follows:

| TREATMENT | CONCEN-TRATION | NO. OF RECORDED MEASURE-MENTS | MEAN SURVIVING FRACTION |
| --- | --- | --- | --- |
| untreated | — | 1 | 24.8% |
| n-propanol | 5 mM | 1 | 48.7% |
| i-propanol | 5 mM | 1 | 34.3% |
| n-butanol | 5 mM | 1 | 47.9% |
| 2,3 n-butenol | 5 mM | 1 | 8.6% |
| 3,4 n-butenol | 5 mM | 1 | 29.3% |
| t-butanol | 5 mM | 1 | 35.9% |
| ethanol | 20 mM | 1 | 49.2% |

The above data illustrates the effectiveness of various primary aliphatic alcohols in alleviating ischemic-reperfusion injury. This data illustrates that the primary aliphatic alcohols are more effective than their related analogues. This suggests the importance of steric and electronic factors which probably determine ligand-receptor affinity.

EXAMPLE 5

Using the procedure set forth in Example 1, the survival of untreated hepatocytes was compared with the survival of hepatocytes treated with various agents at equimolar aqueous concentrations (5 mM). Measurements from five (5) observations were recorded. The mean surviving fraction of hepatocytes were as follows:

| TREATMENT | NO. OF RECORDED MEASUREMENTS | MEAN SURVIVING FRACTION |
|---|---|---|
| untreated | 5 | 32.80 ± 6.71% |
| ethanol | 5 | 62.14 ± 10.0% |
| n-propanol | 5 | 66.84 ± 9.89% |
| n-butanol | 5 | 68.50 ± 9.89% |
| n-pentanol | 5 | 71.94 ± 9.58% |
| n-hexanol | 5 | 51.48 ± 19.05% |

The above data illustrates the effectiveness of the primary aliphatic alcohols in alleviating ischemic-reperfusion injury.

EXAMPLE 6

Using the procedure set forth in Example 1, the survival of untreated hepatocytes was compared with the survival of hepatocytes treated with various therapeutic agents at equimolar membrane concentrations (0.15 mmol/kg membrane). Measurements from 4 to 5 observations were recorded. The mean surviving fraction of hepatocytes were as follows:

| TREATMENT | NO. OF RECORDED MEASUREMENTS | MEAN SURVIVING FRACTION |
|---|---|---|
| untreated | 5 | 32.80 ± 6.71% |
| ethanol | 4 | 60.43 ± 8.26% |
| n-propanol | 4 | 49.55 ± 8.17% |
| n-butanol | 4 | 40.68 ± 11.37% |
| n-pentanol | 4 | 35.08 ± 11.83% |
| n-hexanol | 4 | 31.43 ± 8.83% |

The above data, when taken in combination with the data reported in Example 5, suggests that the activity of the primary aliphatic alcohols in alleviating ischemic-reperfusion injury is not confined to the cellular membrane system.

EXAMPLE 7

Using the procedure set forth in Example 1, the survival of untreated hepatocytes was compared with the survival of hepatocytes treated with various agents. Measurements from four (4) observations were recorded. The mean surviving fraction of hepatocytes were as follows:

| TREATMENT | CONCENTRATION | NO. OF RECORDED MEASUREMENTS | MEAN SURVIVING FRACTION |
|---|---|---|---|
| untreated | — | 4 | 25.08 ± 2.45% |
| 2-phenylethanol | 10 mM | 4 | 47.78 ± 3.84% |
| ethanol | 20 mM | 4 | 49.60 ± 2.09% |

The above data illustrates the activity of a preferred aliphatic alcohol (ethanol) therapeutic agent of the present invention and a preferred phenylalcohol (2-phenylethanol) therapeutic agent of the present invention in alleviating ischemic-reperfusion injury.

EXAMPLE 8

Using the procedure set forth in Example 1, the survival of untreated hepatocytes was compared with the survival of hepatocytes treated with various therapeutic agents. Measurements from one (1) observation were recorded. The mean surviving fraction of hepatocytes were as follows:

| TREATMENT | CONCENTRATION | NO. OF RECORDED MEASUREMENTS | MEAN SURVIVING FRACTION |
|---|---|---|---|
| untreated | — | 1 | 27.3% |
| 2-phenylethanol | 1 mM | 1 | 36.7% |
| 2-phenylethanol | 2.5 mM | 1 | 43.5% |
| 2-phenylethanol | 5 mM | 1 | 46.5% |
| 2-phenylethanol | 10 mM | 1 | 46.5% |
| ethanol | 20 mM | 1 | 52.5% |

The above data further illustrates the effectiveness of 2-phenylethanol and ethanol in alleviating ischemic-reperfusion injury at a variety of concentrations.

EXAMPLE 9

Using the procedure set forth in Example 1, the survival of untreated hepatocytes was compared with the survival of hepatocytes treated with various agents. Measurements from one (1) observation were recorded. The mean surviving fraction of hepatocytes were as follows:

| TREATMENT | CONCENTRATION | NO. OF RECORDED MEASUREMENTS | MEAN SURVIVING FRACTION |
|---|---|---|---|
| untreated | — | 1 | 28.1% |
| 3-phenylpropanol | 10 mM | 1 | 0% |
| 4-phenylbutanol | 10 mM | 1 | 0% |
| ethanol | 20 mM | 1 | 86.8% |

The above data further illustrates the effectiveness of ethanol in alleviating ischemic-reperfusion injury. The data also illustrates that phenylalcohols having more than 2 carbon atoms in the alcohol portion of the phenylalcohol are ineffective in alleviating ischemic-reperfusion injury but rather contribute to further cell death.

EXAMPLE 10

Using the procedure set forth in Example 1, the survival of untreated hepatocytes was compared with the survival of hepatocytes treated with various therapeutic agents. Measurements from one (1) observation were recorded. The mean surviving fraction of hepatocytes were as follows:

| TREATMENT | CONCENTRATION | NO. OF RECORDED MEASUREMENTS | MEAN SURVIVING FRACTION |
|---|---|---|---|
| untreated | — | 1 | 41.4% |
| sorbitol | 10 mM | 1 | 66% |
| sorbitol | 20 mM | 1 | 64% |
| sorbitol | 30 mM | 1 | 70% |
| ethanol | 20 mM | 1 | 79% |

The above data illustrates the effectiveness of a preferred therapeutic agent of the present invention, sorbitol, at various concentrations in alleviating ischemic-reperfusion injury. The data also further illustrates the effectiveness of ethanol in alleviating ischemic-reperfusion injury.

EXAMPLE 11

Using the procedure set forth in Example 1, the survival of untreated hepatocytes was compared with the survival of hepatocytes treated with various therapeutic agents. Measurements from one (1) observation were recorded. The mean surviving fraction of hepatocytes were as follows:

| TREATMENT | CONCENTRATION | NO. OF RECORDED MEASUREMENTS | MEAN SURVIVING FRACTION |
| --- | --- | --- | --- |
| untreated | — | 1 | 25.4% |
| ethanol | 20 mM | 1 | 46.9% |
| sorbitol | 50 mM | 1 | 45.7% |
| sorbitol | 25 mM | 1 | 47.4% |
| sorbitol | 10 mM | 1 | 40.5% |
| sorbitol | 5 mM | 1 | 43.6% |
| sorbitol | 2.5 mM | 1 | 42.6% |
| sorbitol | 1.0 mM | 1 | 42.3% |
| sorbitol | .5 mM | 1 | 39.3% |
| sorbitol | .25 mM | 1 | 47.6% |
| sorbitol | .1 mM | 1 | 32.9% |

The above data further illustrates the effectiveness of sorbitol at various concentrations in alleviating ischemic-reperfusion injury. The data also further illustrates the effectiveness of ethanol in alleviating ischemic-reperfusion injury.

EXAMPLE 12

Using the procedure set forth in Example 1, the survival of untreated hepatocytes was compared with the survival of hepatocytes treated with various therapeutic agents. Measurements from two (2) observations were recorded. The mean surviving fraction of hepatocytes were as follows:

| TREATMENT | CONCENTRATION | NO. OF RECORDED MEASUREMENTS | MEAN SURVIVING FRACTION |
| --- | --- | --- | --- |
| untreated | — | 2 | 27.7% |
| sorbitol | 5.0 mM | 2 | 56.6% |
| sorbitol | 0.5 mM | 2 | 36.0% |
| sorbitol | 0.05 mM | 2 | 33.8% |
| sorbitol-6-phosphate | 5.0 mM | 2 | 63.7% |
| sorbitol-6-phosphate | 0.5 mM | 2 | 44.9% |
| sorbitol-6-phosphate | 0.05 mM | 2 | 39.3% |
| mannitol | 5.0 mM | 2 | 35.3% |
| mannitol-1-phosphate | 5.0 mM | 2 | 57.7% |

The above data further illustrates the effectiveness of preferred therapeutic agents of the present invention, sorbitol-6-phosphate and mannitol-1-phosphate, at various concentrations in alleviating ischemic-reperfusion injury.

It will be apparent to those skilled in the art that various modifications and variations can be made in the present invention without departing from the scope or spirit of the invention. Thus, it is intended that the present invention cover the modifications and variations of this invention provided that they come within the scope of the appended claims or their equivalents.

What is claimed is:

1. A method for alleviating ischemic-reperfusion injury in tissue in a mammal where said tissue has suffered from a deprivation of oxygen comprising administering to said mammal as the active reperfusion injury alleviating ingredient an amount of a primary aliphatic alcohol having from 2 to 6 carbon atoms concurrent with or during the restoration of oxygen in an amount effective to alleviate intracellular parenchymal cell damage when the cell is resupplied with oxygen.

2. The method of claim 1 wherein said primary aliphatic alcohol has from 2 to 5 carbon atoms.

3. The method of claim 2 wherein said primary aliphatic alcohol is ethanol.

4. The method of claim 2 wherein said primary aliphatic alcohol is n-propanol.

5. The method of claim 2 wherein said primary aliphatic alcohol is n-butanol.

6. The method of claim 2 wherein said primary aliphatic alcohol is n-pentanol.

* * * * *